United States Patent
Aubrun et al.

(10) Patent No.: US 9,901,524 B2
(45) Date of Patent: Feb. 27, 2018

(54) FOAMING COMPOSITION COMPRISING AT LEAST ONE GLYCINATE TYPE SURFACTANT

(71) Applicant: L'OREAL, Paris (FR)

(72) Inventors: Odile Aubrun, Antony (FR); Mahassine Safouane, Paris (FR); Caroline Mena, Paray Vieille Poste (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/036,221

(22) PCT Filed: Nov. 12, 2014

(86) PCT No.: PCT/EP2014/074360
§ 371 (c)(1),
(2) Date: May 12, 2016

(87) PCT Pub. No.: WO2015/071298
PCT Pub. Date: May 21, 2015

(65) Prior Publication Data
US 2016/0296442 A1  Oct. 13, 2016

(30) Foreign Application Priority Data
Nov. 13, 2013  (FR) ..................... 13 61086

(51) Int. Cl.

| | | |
|---|---|---|
| *C11D 1/10* | (2006.01) | |
| *C11D 1/88* | (2006.01) | |
| *C11D 7/24* | (2006.01) | |
| *A61K 8/06* | (2006.01) | |
| *A61K 8/31* | (2006.01) | |
| *A61K 8/34* | (2006.01) | |
| *A61K 8/36* | (2006.01) | |
| *A61K 8/40* | (2006.01) | |
| *A61K 8/44* | (2006.01) | |
| *A61Q 1/14* | (2006.01) | |
| *A61Q 5/02* | (2006.01) | |
| *A61Q 19/10* | (2006.01) | |
| *A61K 8/81* | (2006.01) | |
| *A61K 8/04* | (2006.01) | |
| *A61K 8/46* | (2006.01) | |

(52) U.S. Cl.
CPC ................ *A61K 8/44* (2013.01); *A61K 8/046* (2013.01); *A61K 8/062* (2013.01); *A61K 8/31* (2013.01); *A61K 8/361* (2013.01); *A61K 8/442* (2013.01); *A61K 8/466* (2013.01); *A61K 8/8111* (2013.01); *A61Q 1/14* (2013.01); *A61Q 5/02* (2013.01); *A61Q 19/10* (2013.01); *A61K 2800/48* (2013.01); *A61K 2800/54* (2013.01); *A61K 2800/594* (2013.01); *A61K 2800/596* (2013.01); *A61K 2800/5922* (2013.01)

(58) Field of Classification Search
CPC .... C11D 1/10; C11D 1/88; C11D 7/24; A61K 8/06; A61K 8/31; A61K 8/34; A61K 8/36; A61K 8/40; A61K 8/44; A61Q 1/14; A61Q 5/02; A61Q 19/10
See application file for complete search history.

(56) References Cited

U.S. PATENT DOCUMENTS

| | | | | |
|---|---|---|---|---|
| 2011/0086789 A1* | 4/2011 | Tsaur | ..................... | A61K 8/361 510/129 |
| 2011/0275552 A1 | 11/2011 | Patel et al. | | |
| 2012/0094885 A1* | 4/2012 | Liu | ........................ | A61K 8/361 510/159 |

FOREIGN PATENT DOCUMENTS

| | | |
|---|---|---|
| JP | 2014-009195 A | 1/2014 |
| KR | 2008-0063898 A | 7/2008 |
| WO | WO-2013/042274 A1 | 3/2013 |

* cited by examiner

*Primary Examiner* — Brian P Mruk
(74) *Attorney, Agent, or Firm* — Polsinelli PC

(57) ABSTRACT

This invention relates to a composition comprising at least the following in a physiologically acceptable medium:
  an aqueous phase and;
  an oily phase comprising at least one non-volatile hydrocarbon oil chosen from among linear or branched hydrocarbons, and;
  at least one glycinate type anionic surfactant and
  possibly at least one additional anionic surfactant different from glycinates and fatty acid salts;
  at least one amphoteric or zwitterionic surfactant and;
  at least 5% by weight of the total weight of the composition of at least one structuring agent chosen from among saturated fatty acids with a melting point of less than 45° C., saturated fatty alcohols with a melting point of less than 45° C., and mixtures thereof and;
  the ratio by weight of the total quantity of anionic surfactants and amphoteric or zwitterionic surfactants to the quantity of the structuring agent varies between 80/20 and 60/40.

19 Claims, No Drawings

FOAMING COMPOSITION COMPRISING AT LEAST ONE GLYCINATE TYPE SURFACTANT

CROSS REFERENCE TO RELATED APPLICATIONS

This application is a National Phase filing under 35 U.S.C. § 371 of PCT/EP2014/074360 filed on Nov. 12, 2014; and this application claims priority to Application No. 1361086 filed in France on Nov. 13, 2013, under 35 U.S.C. § 119. The entire contents of each application are hereby incorporated by reference.

This invention relates to a composition and particularly a cosmetic composition, its method of preparation and its applications in the field of washing compositions.

Some consumers search for cleansing products that also have moisturization benefits. In general, these are creams containing oils. These products have destabilization phenomena: phase shift or fluidization at low temperature and their foaming capacity remains low.

There is still a need for compositions for cleaning keratin materials containing at least one oil, and that remain stable after at least 2 months storage under temperature conditions varying from 4 to 45° C., and particularly for which the loss of viscosity compared with the initial viscosity is less than 30%. These compositions should also have good foaming properties (good start).

International application WO 2012049025 discloses liquid compositions for cleansing the body that remain stable for 7 days at 4° C. Their stability is evaluated by measuring the viscosity. This composition contains 0.1 to 5% of hydrogenated triglyceride which makes it stable, and a mixture of anionic, non-ionic and amphoteric surfactants (TA), preferably an isethionate and/or a glycinate. This type of composition cannot be used to achieve satisfactory stability in storage particularly after two months at 4° C., at ambient temperature and at 45° C.

International application WO 01/19949 discloses cleansing compositions comprising a lamellar phase with a low concentration of salt (NaCl) (less than 1.1%). These compositions contain:
- a surfactant system with an amphoteric, zwitterionic surfactant or a mixture thereof, and an anionic surfactant;
- a lamellar phase structuring agent among the group composed of fatty acids, fatty esters, trihydroxystearine or mixtures thereof;
- a strong electrolyte with a sufficient concentration to maintain a minimum of at least 65% of the initial viscosity during cold storage (1-3 "freezing" cycles between −17.8 and 21° C.).

The viscosity is measured using a T-bar spindle A. The initial viscosity is 15000 to 300000 cps. Production of compositions containing less than 1.1% salt (NaCl) is a severe constraint on the formulation in that most commercial surfactants contain a high concentration of salt (NaCl).

International application WO 0059454 discloses liquid cleansing compositions with improved stability at low temperature, and containing a particular mixture of anionic surfactants, at least one of which is branched (e.g. acyl isethionate). The viscosity is measured after 1-3 "freezing" cycles between −17.8 and 21° C. It is initially between 20000 and 300000 cps, and its variation in time must be less than 35%. This type of composition imposes the presence of particular branched surfactants; which considerably reduces the range of possible formulations.

American patent U.S. Pat. No. 6,077,816 applies to liquid cleansing compositions containing soluble lamellar phases. These compositions contain anionic surfactants (e.g. isethionate and/or sulfosuccinate). Structuring agents such as unsaturated liquid fatty acids in $C_8$-$C_{24}$ and/or branched fatty acids in the oleic/isostearic acids group and mixtures thereof. In these formulations it is observed that the presence of long chain fatty acids has a negative impact on the foam quality (good start).

The purpose of the invention is to provide a composition, and particularly a cosmetic composition, capable of solving the technical problems presented above.

In particular, the purpose of the invention is to provide a cleansing composition capable of forming a lamellar phase, comprising at least one oil and at least one structuring agent that has good foaming performances (particularly good start) and that is stable from 4 to 45° C. after a period of at least two months, particularly for which the loss of viscosity from the initial viscosity is less than 30%.

The inventors discovered that stable compositions can be obtained capable of forming a lamellar phase with good foaming performances and which are stable from 4 to 45° C. for at least 2 months, particularly for which the loss of viscosity from the initial viscosity is less than 30%, using combinations of specific surfactants, specific oils and particular structuring agents.

Thus, this invention applies to a composition containing at least one glycinate type surfactant, an amphoteric surfactant, a non-volatile hydrocarbon oil chosen from among linear or branched hydrocarbons, and at least 5% by weight of the total weight of the composition of at least one structuring agent chosen from among saturated fatty acids with a melting point of less than 45° C., saturated fatty alcohols with a melting point of less than 45° C., and mixtures thereof;

A first aspect of this invention applies to a composition comprising at least the following in a physiologically acceptable medium:
- an aqueous phase and;
- an oily phase comprising at least one non-volatile hydrocarbon oil chosen from among linear or branched hydrocarbons, and;
- at least one glycinate type anionic surfactant and
- possibly at least one additional anionic surfactant different from glycinates and fatty acid salts;
- at least one amphoteric or zwitterionic surfactant and;
- at least 5% by weight of the total weight of the composition of at least one structuring agent chosen from among saturated fatty acids with a melting point of less than 45° C., saturated fatty alcohols with a melting point of less than 45° C., and mixtures thereof;
- the ratio by weight of the total quantity of anionic surfactants and amphoteric or zwitterionic surfactants to the quantity of the structuring agent varies between 80/20 and 60/40.

Another subject of the invention consists of cosmetic use of the composition as defined according to this invention, as a cleansing product and/or for makeup removal for keratin materials.

Another subject of this invention consists of a cosmetic method of cleaning dirt residues of human keratin materials, characterized by the fact that the composition of the invention is applied on said keratin materials in the presence of water, and massage is performed to create a foam and the foam formed and the dirt residues are eliminated by rinsing with water.

"Total quantity of anionic surfactants and amphoteric or zwitterionic surfactants" refers to the quantity of all amphoteric or zwitterionic surfactants present in the composition and all anionic surfactants present in the composition, namely the glycinate type surfactant(s), the additional anionic surfactant(s) other than glycinates and fatty acid salts.

"Quantity of structuring agent" refers to the quantity of structuring agent chosen from among saturated fatty acids with a melting point of less than 45° C., saturated fatty alcohols with a melting point of less than 45° C., and mixtures thereof.

"Human keratin materials" refers to the skin (body, face, eye contour), hair, eyelashes, eyebrows, body hair, nails, lips, mucous membranes.

"Physiologically acceptable" means being compatible with the skin and/or its appendages, having a pleasant color, odor and touch and that does not generate any unacceptable discomfort (tickling, tightness, rash) that might discourage a consumer from using this composition.

"Structuring agent" means any compound that enables the organization of surfactants in mesophase such as lamellar phases thickening the medium.

"Saturated fatty acid" refers to any carboxylic acid comprising a linear saturated hydrocarbon chain (without any double or triple covalent bond), particularly composed of a linear alkyl chain, said chain comprising at least 8 carbon atoms and a carboxylic (COOH) function.

According to one particular embodiment of the invention, said fatty acid may be in a partially or totally salt form, particularly it may be partially or totally neutralized by an inorganic or organic base with pH values more than 5.0.

The inorganic base used to neutralize the fatty acid is usually chosen from among alkaline metal hydroxides such as soda or potash, hydroxides of alkaline-earth metals or ammonia.

The organic base may for example be an alkanolamine such as monoethanolamine, triethanolamine, etc.

"Saturated fatty alcohol" means any alcohol comprising a linear saturated hydrocarbon chain (without double or triple covalent bond), particularly composed of an linear alkyl chain, said chain comprising at least 8 carbon atoms and a hydroxyl function.

"Hydrocarbon chain" refers to an organic group composed predominantly of hydrogen atoms and carbon atoms.

"Hydrocarbon" means any organic compound containing essentially carbon (C) and hydrogen (H) atoms. It usually has a molecular formula of the type CnHm, where n and m are two integers.

"Included between X and Y" means the range of values between the X and Y limits inclusive.

The compositions according to the invention are stable for more than two months from 4° C. and 45° C. and have good foaming properties. In particular, a composition according to the invention has a good foam quality and good stability for at least two months from 4 to 45° C., maintaining more than 70% of its initial viscosity at 45° C. and more than 60% of its initial viscosity at 4° C.

The use of a glycinate type surfactant enables better stability and better foaming capacity.

The ratio by weight between the anionic surfactant(s) and the amphoteric surfactant(s) preferably varies between 20/80 and 75/25, and preferably between 25/75 and 55/45.

Throughout the remaining description, the nature of ingredients is usually given under the term INCI.

The foaming composition according to the invention contains a surfactant system that is responsible for the foaming nature of the composition.

Foaming surfactants are detergents and are differentiated from emulsifiers by the values of their HLB (Hydrophilic Lipophilic Balance), the HLB being the ratio between the hydrophilic part and the lipophilic part in the molecule. The term HLB is well known to those skilled in the art and is described for example in "The HLB system. A time-saving guide to Emulsifier Selection" (published by ICI Americas Inc; 1984). For emulsifiers, the HLB will usually be between 3 and 8 for the preparation of W/O emulsions and 8 to 18 for preparation of O/W emulsions, while the HLB value of foaming surfactants is usually more than 20. The HLB or hydrophilic-lipophilic balance of the surfactant(s) used according to the invention can be determined using the GRIFFIN method or the DAVIES method.

Anionic glycinate type surfactants according to the invention are typically chosen from among alkyl glycinates with the following chemical formula:

where R is an alkyl chain with 8 to 16 carbon atoms.

Preferably, alkyl glycinates according to the invention are chosen from among N-sodium cocoyl glycinate (for example AMILITE GCS-12® or AMILITE GCK 12 by AJINOMOTO) sodium N-cocoyl glycinate (for example HOSTAPON SG by Clariant), and any one of their mixtures.

The composition may contain one or several other anionic surfactants such as:

acyl glutamates with formula:

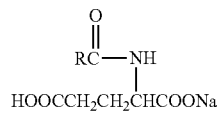

Glutamates, like triethanolamine mono-cocoyl glutamate marketed under the name ACYLGLUTAMATE CT-12® by the Ajinomoto company, triethanolamine lauroylglutamate marketed under the name ACYLGLUTAMATE LT-12® by the Ajinomoto company, in particular, disodium cocoyl glutamate (for example AMISOFT), triethanolamine mono-cocoyl glutamate;

alkyl isethionates with formula:

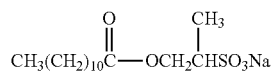

Isethionates include acylisethionates such as sodium cocoyl-isethionate, such as the product marketed under the name JORDAPON CI P® by the Jordan company. In particular, sodium Lauroyl methyl isethionate (for example ISELUX LQ-CLR-SB by INNOSPEC);

alkyl sulfosuccinate with formula:

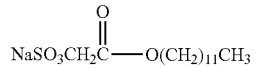

Sulfosuccinates include for example oxyethylene laurylic alcohol mono-sulfosuccinate (C12/C14 70/30) (3 OE) marketed under the names SETACIN 103 SPECIAL®, REWOPOL SB-FA 30 K 4® by the Witco company, disodium salt of an alcohol hemi-sulfosuccinate C12-C14 marketed under the name SETACIN F SPECIAL PASTE® by the Zschimmer Schwarz company, oxyethylene disodium oleamidosulfosuccinate (2 OE) marketed under the name STANDAPOL SH 135® by the Cognis company, lauric amide oxyethylene mono-sulfosuccinate (5 OE) marketed under the name LEBON A-5000® by the Sanyo company, di-sodium salt of lauryl citrate oxyethylene mono-sulfosuccinate (10 OE) marketed under the name REWOPOL SB CS 50® by the Witco company, ricinoleic mono-ethanolamide mono-sulfosuccinate marketed under the name REWODERM S 1333® by the Witco company. Polydimethylsiloxane sulfosuccinates such as disodium dimethicone sulfosuccinate PEG-12 marketed under the name MACKANATE-DC30 by the Mac Intyre company can also be used;

alkyl sulfoacetates, such as sodium salt of lauryl sulfoacetate under the name INCI SODIUM LAURYL SULFOACETATE and marketed under the name LATHANOL LAL® by the STEPAN company.

alkyl taurate with formula:

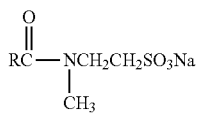

j) Taurates include sodium salt of palm oil methyltaurate marketed under the name HOSTAPON CT PATE® by the Clariant company; N-acyl N-methyltaurates such as sodium N-cocoyl N-methyltaurate marketed under the name HOSTAPON LT-SF® by the Clariant company or marketed under the name NIKKOL CMT-30-T® by the Nikkol company, sodium palmitoyl methyltaurate marketed under the name NIKKOL PMT® by the Nikkol company;

alkyl sulfates and alkyl ether sulfates such as compounds with formulas:

and

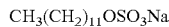

Alkyl sulfates include for example sodium lauryl sulfate (CTFA name sodium lauryl sulfate) such as the product marketed by the Tensachem company under the name TENSOPOL USP94, triethanolamine lauryl sulfate (CTFA name TEA-lauryl sulfate) such as the product marketed by the Huntsman company under the name EMPICOL TL40 FL or the product marketed by the Cognis company under the name TEXAPON T42, products that are 40% in aqueous solution. There is also ammonium lauryl sulfate (CFTA name Ammonium lauryl sulfate) such as the product marketed by the Huntsman company under the name EMPICOL AL 30FL that is 30% in aqueous solution.

Alkyl ether sulfates include for example sodium laureth sulfate (CTFA name sodium laureth sulfate) like that marketed under the names TEXAPON N40 and TEXAPON AOS 225 UP by the Cognis company, ammonium laureth sulfate (CTFA name ammonium laureth sulfate) like that marketed under the name STANDAPOL EA-2 by the Cognis company.

It may be any mixture of the above-mentioned anionic surfactants.

Preferably, the additional anionic surfactant is chosen from among alkyl sulfates, alkyl ether sulfates such as sodium laureth sulfate, alkyl isethionates, alkyl sulfoacetates or mixtures thereof.

Preferably, the composition according to the invention includes glycinate type surfactant(s) with a content of at least 30% by weight of the total weight of the anionic surfactant(s) present in the composition, and preferably more than 50% by weight.

The amphoteric or zwitterionic surfactants may be chosen from among for example betaines, N-alkylamidobetaines or derivatives thereof, sultaines, alkyl polyaminocarboxylates, alkylamphoacetates and mixtures thereof.

Betaines include particularly alkylbetaines for example such as cocobetaine like the product marketed under the name DEHYTON AB-30® by the Cognis company, laurylbetaine such as the product marketed under the name GENAGEN KB® by the Clariant company, oxyethylene laurylbetaine (10 OE) such as the product marketed under the name LAURYLETHER (10 OE) BETAINE® by the Shin Nihon Rica company, oxyethylene stearylbetaine (10 OE) such as the product marketed under the name STEARYLETHER (10 OE) BETAINE® by the Shin Nihon Rica company.

Example of N-alkylamidobetaines and derivatives thereof include cocamidopropyl betaine marketed under the name LEBON 2000 HG® by the Sanyo company, or marketed under the name EMPIGEN BB® by the Albright & Wilson company, lauramidopropyl betaine marketed under the name REWOTERIC AMB12P® by the Witco company.

Sultaines include hydroxylsultaines like Cocamidopropyl hydroxysultaine such as the product marketed under the name REWOTERIC AM CAS by the Golschmidt-Degussa company, or the product marketed under the name CROSULTAINE C-50® by the Croda company.

Alkyl polyaminocarboxylates (APAC) include sodium cocoylpolyamino-carboxylate marketed under the name AMPHOLAK 7 CX/C®, and AMPHOLAK 7 CX® by the Akzo Nobel company, sodium stearyl-polyamidocarboxylate marketed under the name AMPHOLAK 7 TX/C by the Akzo Nobel company, sodium carboxymethyloleyl-polypropylamine marketed under the name AMPHOLAK XO7/C® by the Akzo Nobel company.

Alkylamphoacetates include for example N-disodium N-cocoyl-N-carboxymethoxyethyl-N-carboxymethyl-ethylenediamine (CTFA name disodium cocoamphodiacetate) such as the product marketed under the name MIRANOL C2M CONCENTRE NP® by the Rhodia company, N-sodium N-cocoyl-N-hydroxyethyl-N-carboxymethyl-ethylenediamine (CTFA name sodium cocamphoacetate), sodium cocoamphohydroxypropyl sulfonate marketed under the name MIRANOL CSE by the Rhodia company.

Amphoteric or zwitterionic surfactants according to the invention are preferably chosen from among:

betaine alkyls and particularly Lauryl Betaine (for example GENAGEN KB® by CLARIANT), Coco-betaine (for example Dehyton AB 30 ® by BASF or TEGO Betain AB 1214 ® by Evonik Goldschmidt GmbH);

N-alkylamido betaines and derivatives thereof, and particularly Cocamidopropyl betaine (for example LEBON 2000 HG® by SANYO or EMPIGEN BB® by ALBRIGHT ET WILSON), lauramidopropyl betaine (for example REWOTERIC AMB12P® by WITCO), N-di-sodium N-carboxyethoxyethyl N-cocoylamidoethyl am inoacetate (for example MIRANOL C2M CONCENTRE NP® by RHODIA CHIMIE).

Sultaines such as cocoyl amidopropyl hydroxy-sulfobetaine (for example CROSULTAINE C-50® by CRODA) and any one of their mixtures;

Preferred amphoteric or zwitterionic surfactants according to the invention are chosen from among alkyl betaines and alkyl amidopropylbetaines.

Amphoteric or zwitterionic surfactants used will preferably be Cocamidopropyl betaine, Cocobetaine and mixtures thereof.

The concentration of amphoteric or zwitterionic surfactants is preferably more than or equal to 5% by weight of the total weight of the composition and preferably 5 to 15% by weight. The invention also includes 5% by weight of at least one structuring agent chosen from among saturated fatty acids with a melting point of less than 45° C., saturated fatty alcohols with a melting point of less than 5° C. and mixtures thereof.

The saturated fatty acids and alcohols are preferably in C8-C24 and preferably have a melting point of more than 20° C. and less than 45° C.

For the purposes of the invention, the melting temperature is the temperature of the most endothermic peak observed in thermal analysis (DSC). The melting point of the structuring agent may be measured using a Differential Scanning calorimeter (DSC) by TA instruments—Qserie™ Q100, using the following protocol:

A 5 mg sample of the structuring agent is placed in a crucible. The temperature is at equilibrium at 20° C. for 10 minutes. The temperature of the sample is increased for a first time from 20° C. to 80° C. at a heating rate of 20° C./minute, and is then cooled from 80° C. to −10° C. at a cooling rate of 20° C./minute.

During the temperature rise, the sample absorbs heat and its physical aspect changes from solid to liquid. This absorption of heat is identified by a dip indicating the endothermic nature of the transformation. The melting point is the lowest temperature in the dip.

Preferably, the fatty acid(s) and/or the fatty alcohol(s) according to the invention are present in concentrations varying from 5 to 10% by weight relative to the total weight of the composition and more preferably from 5 to 7% by weight.

Saturated fatty acids according to the invention are preferably lauric acid.

Saturated fatty alcohols according to the invention are preferably lauric alcohol.

Thus advantageously, lauric acid and/or lauric alcohol will be used.

According to one particularly preferred embodiment, the composition according to the invention comprises
an aqueous phase, and;
an oily phase comprising at least Vaseline oil and possibly a polyisobutene and
at least sodium N-cocoyl glycinate and
at least Cocamidopropyl betaine and/or Cocobetaine and
at least 5% by weight of lauric acid as a proportion of the total weight of the composition, and;
the ratio by weight of the total quantity of anionic and amphoteric or zwitterionic surfactants to the quantity of structuring agent varying between 80/20 and 60/40.

Preferably, the total concentration of anionic surfactants, amphoteric surfactants and fatty acid and/or fatty alcohol varies from 12% to 33% by weight and preferably from 15% to 32% by weight, of the total weight of the composition.

The compositions according to the invention contain at least one organic liquid phase immiscible in water, called the oily phase. This usually comprises one or several hydrophobic compounds that make said phase immiscible in water. Said phase is liquid (in the absence of a structuring agent) at ambient temperature (20-25° C.).

The organic liquid phase immiscible in water conforming with the invention comprises at least one non-volatile hydrocarbon oil chosen from among linear or branched hydrocarbons, with an inorganic or synthetic origin.

"Oil" means a liquid fatty body at ambient temperature (25° C.) and atmospheric pressure (760 mm Hg namely $10^5$ Pa).

"Non-volatile oil" means an oil that will remain on the skin or the keratinous fiber for several hours at ambient temperature and atmospheric pressure and particularly with a vapor pressure of less than $10^{-3}$ mm Hg (0.13 Pa).

"Hydrocarbon oil" means an oil comprising mainly carbon and hydrogen atoms and possibly one or several functions chosen from among hydroxyl, ester, ether, carboxylic functions. In general the viscosity of the oil is between 0.5 and 100 000 mPa·s, preferably between 50 and 50 000 mPa·s and even more preferably between 100 and 30 000 mPa·s.

Linear or branched hydrocarbons are preferably chosen from among paraffin oils and derivatives thereof, Vaseline oil, polydecenes, polybutenes, polyisobutenes, hydrogenated polyisobutenes such as Parleam, squalane and more particularly Vaseline oil and/or a polyisobutene.

The compositions according to the invention may also contain other fatty bodies in the oily phase such as
fatty acid triglycerides with 4 to 24 carbon atoms such as triglycerides of caprylic/capric acids such as those sold by the Stearineries Dubois company or sold under the names Miglyol 810, 812 and 818 by the Dynamit Nobel company, shea butter;
esters, particularly fatty acids such as oils with formula $R^1COOR^2$ in which $R^1$ represents the remainder of a superior linear or branched fatty acid comprising 1 to 40 carbon atoms and $R^2$ represents a particularly branched hydrocarbon chain containing 1 to 40 carbon atoms where $R^1+R^2 \geq 10$ such as isononyl isononanoate, isopropyl myristate, isopropyl palmitate, alcohol benzoate in $C_{12}$ to $C_{15}$.
volatile or non-volatile silicone oils.

The total quantity of non-volatile hydrocarbon oils preferably accounts for at least 50% by weight of the oily phase.

The concentration of the oily phase preferably varies from 0.1 to 20% by weight in comparison with the total weight of the composition and more preferably 2 to 14% by weight relative to the total weight of the composition.

According to one particular embodiment of the invention, the composition according to the invention may contain at least one thickening agent.

Thickening agents that may be used include particularly associative polymers.

The term "associative polymers" refers to hydrophilic polymers capable of reversibly combining with each other or with other molecules in an aqueous medium.

Their chemical structure includes more particularly at least one hydrophilic zone and at least one hydrophobic zone.

"Hydrophobic group" means a radical or polymer with a saturated or unsaturated, linear or branched hydrocarbon chain. When it denotes a hydrocarbon radical, the hydrophobic group comprises at least 10 carbon atoms and preferably 10 to 30 carbon atoms, and particularly 12 to 30 carbon atoms.

Preferably, the hydrocarbon group originates from a monofunctional compound.

For example, the hydrophobic group may be derived from a fatty alcohol such as stearylic alcohol, dodecylic alcohol, decylic alcohol or a polyoxyalkylene fatty alcohol such Steareth-100. It may also denote a hydrocarbon polymer for example such as polybutadiene.

Associative polymers conforming with this invention may be anionic, cationic, non-ionic or amphoteric.

According to one preferred embodiment, associative anionic polymers may consist of copolymers comprising among their monomers an unsaturated carboxylic α,β-monoethylenic acid and an unsaturated carboxylic α,β-monoethylenic acid ester and an oxyalkylene fatty alcohol. Preferably, these compounds also include a monomer consisting of an ester of an unsaturated α,β-monoethylenic carboxylic acid and alcohol in C1-C4.

An example of this type of compound is ACULYN 22 (sold by the ROHM & HAAS company, which is a methacrylic acid/ethyl acrylate/oxyalkylene stearyl methacrylate terpolymer (comprising 20 OE patterns) or ACULYN 28 (methacrylic acid/ethyl acrylate/behenyl oxyethylene methacrylate (25OE) terpolymer.

There are also cross-linked acrylate/C10-C30-alkylacrylate copolymers such as PEMULEN TR1® and PEMULEN TR2®, Polyacrylate-33 sold under the trade name RHEOMER 33® by SOLVAY, the copolymer INCI name Acrylates/Vinyl Neodecanoate Crosspolymer sold under the trade name ACULYN 38® by the DOW CHEMICAL company.

Associative anionic polymers also include copolymers comprising a) 2-acrylamido 2-methylpropane sulfonic acid patterns (AMPS®) and b) (meth)acrylates patterns substituted by a polyoxyalkylene alkyl C12-C18 chain such as copolymers with INCI name:

Ammonium Acryloyldimethyltaurate/Laureth-7 Methacrylate Copolymer marketed under the ARTISTOFLEX LNC name by the Clariant company, Ammonium Acryloyldimethyltaurate/Steareth-25 Methacrylate Crosspolymer) (marketed under the ARISTOFLEX HMS name by the Clariant company, Ammonium Acryloyldimethyltaurate/Steareth-8 Methacrylate Copolymer) marketed under the ARISTOFLEX SNC name by the Clariant company, Ammonium Acryloyldimethyltaurate/Beheneth-25 Methacrylate Crosspolymer) under the ARISTOFLEX HMB name by the Clariant company and mixtures thereof Non-ionic associative polymers include:

celluloses modified by groups that comprise at least one fatty chain for example such as hydroxyethylcelluloses modified by groups comprising at least one fatty chain such as alkyl groups, particularly in C8-C22, arylalkyl, alkylaryl, such as NATROSOL PLUS GRADE 330 CS (alkyls in C16) sold by the AQUALON company, celluloses modified by alkyl phenol glycol ether polyalkylene groups such as the AMERCELL POLYMER HM-1500 product (polyethylene glycol (15) nonyl phenol ether) sold by the AMERCHOL company, guars such as hydroxypropyl guar, modified by groups containing at least one fatty chain such as an alkyl chain, inulins modified by groups comprising at least one fatty chain such as alkyl carbamate inulins and particularly lauryl carbamate inulin marketed by the ORAFTI company under the name INUTEC SP1, polyethyleneglycol and fatty acid diesters such as polyethyleneglycol distearate (150 OE) such as PEG-150 distearate sold under the trade name EMCOL L 32-45® by WITCO.

associative polyurethanes such as non-ionic polyether polyurethanes with fatty chain such as Rheolate® FX 1100 (Steareth-100/PEG 136/HDI (hexamethyl diisocyanate) copolymer), Rheolate® 205® with urea function marketed by the ELEMENTIS company or Rheolates® 208, 204 or 212, and Acrysol RM 184® or Acrysol RM 2020. Other examples include the ELFACOS T210® product with alkyl chain in C12-C14 and the ELFACOS T212® product with alkyl chain in C16-18 (PPG-14 Palmeth-60 Hexyl Dicarbamate) from AKZO. The DW 1206B® product from ROHM & HAAS with alkyl chain in C20 and urethane bond marketed with 20% dry material in water, can also be used. Other examples are RHEOLATE® 255, RHEOLATE® 278 and RHEOLATE® 244 sold by the ELEMENTIS company. The DW 1206F product and the DW 1206J product proposed by the ROHM & HAAS company can also be used.

Cationic associative polymers include quaternised alkylhydroxyethyl-celluloses with fatty chains in C8-C30, QUATRISOFT LM 200, QUATRISOFT LM-X 529-18-A, QUATRISOFT LM-X 529-18B (alkyl in C12) and QUATRISOFT LM-X 529-8 (alkyl in C18) products marketed by the AMERCHOL company and CRODACEL QM, CRODACEL QL (alkyl in C12) and CRODACEL QS (alkyl in C18) products marketed by the CRODA company.

Thickening agents according to the invention include modified carboxyvinylic polymers and particularly cross-linked acrylic polyacids, for example Carbomers such as Carbopols®; ethyl acrylate/methacrylic acid copolymer with INCI name: sold under the name CARBOPOL SF1® by the LUBRIZOL company.

Examples of thickening agents according to the invention include starches and particularly distarch phosphates or compounds rich in distarch phosphate and particularly distarch phosphate hydroxypropyl ethers with INCI name: Hydroxypropyl Starch Phosphate such as products sold under the trade names Farinex VA70 C or FARMAL MS 689 ® by the AVEBE Stadex company; products sold under the trade names Structure BTC®, Structure HVS®, Structure XL® or STRUCTURE ZEA® by NATIONAL STARCH (corn distarch phosphate).

Compositions according to the invention may also contain esters, triglycerides and silicone oils, such that non-volatile hydrocarbon oils preferably account for at least 50% by weight of the oily phase.

The composition according to the invention comprises an aqueous medium or an aqueous phase. An aqueous phase means a phase containing water and usually any molecule dissolved in water in the composition.

The concentration of the aqueous phase preferably varies from 45 to 84% by weight relative to the total weight of the composition and more preferably 50 to 80% by weight relative to the total weight of the composition.

The aqueous phase of compositions according to the invention may contain one or several solvents in addition to water, chosen from among mono-alcohols comprising 1 to 6 carbon atoms, polyols and mixtures thereof. Mono-alcohols particularly include ethanol. Polyols particularly include glycerine; glycols such as butylene glycol, isoprene glycol, propylene glycol, polyethylene glycols such as PEG-8; sorbitol; sugar such as glucose, fructose, maltose, lactose, sucrose and mixtures thereof.

When they are present, the quantity of mono-alcohols and polyols in the composition according to the invention may for example vary from 0.01 to 30% by weight and preferably 2 to 25% by weight and even better 4 to 20% by weight, of the total weight of the composition.

Compositions according to this invention may also contain other additives. In particular, the composition according to the invention applies to cosmetic compositions and therefore includes acceptable excipients for keratin materials such as the skin and its appendages.

The compositions according to the invention may particularly contain opacifiers, cationic polymers, chelating agents, glycols, salts, active compounds, typically such as keratolytic active compounds . . . .

The composition according to the invention may contain different hydrosoluble or liposoluble additives chosen typically from among those used in health care or skin makeup removal products, to the extent that these additives and quantities of them do not adversely affect the qualities required for the composition according to the invention.

The cleansing composition according to the invention may also include the following additives: co-surfactants; preservative agents, sequestering agents (EDTA and its salts); antioxidants; fragrances; coloring materials; soluble colorants or encapsulated or non-encapsulated pigments; conditioning agents, thickening, anionic, non ionic, cationic or amphoteric polymers.

The quantities of these various additives are conventionally the quantities used in the domain considered, for example active material is from 0.01 to 40% of the total weight of the composition and preferably from 0.01 to 20%. These additives and their quantities must be such that they do modify the property required for the composition according to the invention.

Among the conditioning agents, the composition may also include a polymeric quartenary ammonium salt.

These compounds can increase the foam quantity and give a sensation of softness and comfort on the skin (moisturization maintained).

Polymeric quaternary ammonium salts are cationic or amphoteric polymers containing at least one atom of quaternised nitrogen. Examples of polymeric quaternary ammonium salts include particularly Polyquaternium (CTFA name), that makes the foaming cream soft and smooth. These polymers may preferably be chosen from among the following polymers:

Polyquaternium 5 such as the MERQUAT 5 product marketed by the NALCO company;

Polyquaternium 6 such as the SALCARE SC 30 product marketed by the CIBA company and the MERQUAT 100 product marketed by the NALCO company;

Polyquaternium 7 such as the MERQUAT S, MERQUAT 2200 and MERQUAT 550 products marketed by the NALCO company and the SALCARE SC 10 product marketed by the CIBA company;

Polyquaternium 10 such as the Polymer JR400 product marketed by the AMERCHOL company;

Polyquaternium 11 such as the GAFQUAT 755, GAFQUAT 755N and GAFQUAT 734 products marketed by the ISP company;

Polyquaternium 15 such as the ROHAGIT KF 720 F product marketed by the ROHM company;

Polyquaternium 16 such as the LUVIQUAT FC905, LUVIQUAT FC370, LUVIQUAT HM552 and LUVIQUAT FC550 products marketed by the BASF company;

Polyquaternium 22 such as the MERQUAT 280 product marketed by the NALCO company;

Polyquaternium 28 such as the STYLEZE CC10 product marketed by the ISP company;

Polyquaternium 39 such as the MERQUAT PLUS 3330 and MERQUAT 3330PR products marketed by the NALCO company;

Polyquaternium 44 such as the LUVIQUAT CARE product marketed by the BASF company;

Polyquaternium 46 such as the LUVIQUAT HOLD product marketed by the BASF company;

Polyquaternium 47 such as the MERQUAT 2001 product marketed by the NALCO company.

Preferably, the polymeric quaternary ammonium salts are chosen from among Polyquaternium-6, Polyquaternium-7, Polyquaternium-39, and mixtures thereof.

The quantity of polymeric quaternary ammonium salts (in active material) may for example vary from 0.01 to 5% by weight or better from 0.05 to 1% by weight of the total weight of the composition.

One example of a particular conditioning agent is Polyquaternium-39, marketed particularly by the NALCO company under the names Merquat Plus 3330 and Merquat 3330PR.

According to one particular embodiment, a composition according to the invention may comprise:
50 to 80% by weight of water;
5 to 25% by weight of an oily phase comprising at least one non-volatile hydrocarbon oil;
5 to 10% by weight of at least one glycinate type anionic surfactant;
5 to 10% by weight of at least one amphoteric surfactant;
at least 5% by weight of a structuring agent chosen from among saturated fatty acids with a melting point of less than 45° C., saturated fatty alcohols with a melting point of less than 45° C., and mixtures thereof;
at least 1% by weight of a thickening agent; said quantities being defined relative to the total weight of the composition.

The invention specifically concerns compositions including:
5 to 20% by weight of Vaseline oil, possibly 1 to 10% of glycerine, possibly 0.01 to 2% by weight of polyethyleneglycol, 50 to 80% of water, 1 to 5% by weight of ACRYLATES/VINYL NEODECANOATE CROSSPOLYMER, 0 to 10% by weight of COCO-BETAINE (30% MA), from 5 to 10%, by weight and preferably from 5 to 8% of lauric acid, from 5 to 10% by weight of SODIUM COCOYL GLYCINATE, from 5 to 10% by weight of cocamidopropyl betaine, from 0.01 to 2% by weight of POLYQUATERNIUM-39, and from 0.01 to 2% by weight of POLYQUATERNIUM-6. Said quantities being defined relative to the total weight of the composition.

More particularly, this invention relates to a foaming composition and more particularly a foaming cosmetic composition. This foaming composition may be intended particularly for washing or cleansing the skin or skin appendages.

Typically, compositions according to this invention are formulated in the form of a physiologically acceptable medium. For the purposes of this invention, a "physiologically acceptable medium" means a medium suitable for the administration of a composition using a topical pathway. Therefore the invention concerns physiologically acceptable formulations.

A physiologically acceptable medium is preferably a cosmetically or dermatologically acceptable medium, in other words odorless, without any unpleasant appearance, and that is perfectly compatible with the topical administration pathway.

Such a medium is considered particularly as being physiologically acceptable when it does not cause any itching, skin tightness or unacceptable rash for the user.

Compositions according to the invention are typically rinsing compositions (rinsing with water or a tonic) and can be used for makeup removal for cleaning human keratin materials such as facial skin or body skin, hair including the scalp, and mucous membranes such as the lips. They may also be care products for example rinse-off masks (in the normal manner in which these products are used).

The invention also relates to the cosmetic use of a composition as defined above, such as a cleansing product and/or a makeup removal product for keratin materials.

The invention also relates to a cosmetic method of cleansing dirt residues from keratin materials, characterized by the fact that a composition as defined in any one of the above claims is applied onto said keratin materials in the presence of water, that a foam is formed by massing and the foam formed together with the dirt residues are eliminated by rinsing with water.

The invention more particularly concerns a cleansing or washing cosmetic care method comprising application of a composition according to the invention. A composition according to the invention can be applied to an area of the skin or the appendages (particularly hair), and foam is formed for example by rubbing and then after a certain time (usually a few tens of seconds or a few minutes), the application zone can be rinsed to eliminate the composition from the zone of the skin or appendages concerned. The application time of the composition before rinsing is adapted to good cleansing or washing of the zone concerned.

This invention will now be described more specifically through examples that are in no way limitative of the scope of the invention. However, the examples provide information about specific characteristics, variants and preferred embodiments of the invention.

In the examples, the temperature is given in degrees Celsius and is the ambient temperature (20-25° C.), unless mentioned otherwise, and the pressure is the atmospheric pressure at sea level unless mentioned otherwise. Furthermore, percentages are given in mass relative to the total mass, unless mentioned otherwise.

In one particularly preferred embodiment, the compositions according to the invention are oil-in-water emulsions, namely in which the discontinuous oily phase is dispersed in the continuous aqueous phase, said phases preferably forming a macroscopically homogeneous composition.

Preparation of Compositions

The compositions according to the invention may be prepared using conventional techniques for the preparation of oil/water emulsions.

In particular they can be obtained using a method including the following steps:
preparation of the fatty phase containing oils at temperatures varying from 50 to 100° C.;
preparation of the aqueous phase containing the anionic surfactant(s), the amphoteric surfactant(s) and the structuring agent at a temperature varying from 50 to 100° C.
mix of the two phases by incorporation of the fatty phase into the aqueous phase at a temperature varying from 50 to 100° C., with mechanical stirring to form an oil-in-water emulsion;
cooling of the emulsion thus obtained to a temperature varying from 20 to 25° C.;
optional addition of additives.

Preferably, the step in which the fatty phase is incorporated into the aqueous phase is made with mechanical stirring using a blade or spiral or rotor-stator type homogenizer. This step is usually done at a speed varying from 300 to 1 000 rev/minute (for example 400) for example for 10-15 minutes.

Preferably, the composition obtained is cooled with slow stirring using scraper blades moving at a speed of less than 1000 rpm.

EXAMPLE COMPOSITIONS

Manufacturing Protocol

The composition according to the invention is composed of:
A fatty phase containing oils and polyethylene glycol. The ingredients are mixed at 85° C.
A first aqueous phase containing anionic, amphoteric surfactants and the structuring agent. The mix is made at a temperature higher than 45° and is cooled to ambient temperature.

The fatty phase is then incorporated while stirring for 10 min at T=400 rpm. The cationic polymers are incorporated at the end of the formulation after mixing the fatty and aqueous phases.

Characterization

The viscosity range of the compositions is from 800 to 15000 mP·s.

The viscosity of the products is measured using a Rheomat 180 viscometer at ambient temperature with a spindle 3 or 4, the rotation speed is 200 rpm and the measurement time is 10 minutes.

The stability is evaluated according to the variation in viscosity of the sample in time and the macroscopic aspect (homogeneous, phase shift):
δ ($\eta 0$-$\eta 45$) 2 months is the percentage in absolute value of the variation between the viscosity measurement at t=24 h at ambient temperature and the viscosity measurement after 2 months at 45° C.
δ ($\eta 0$-$\eta 4$) 2 months is the percentage in absolute value of the variation between the viscosity measurement at t=24 h at ambient temperature and the viscosity measurement after 2 months at 4° C.

R(surfactant/structuring agent) is the mass ratio between the sum of amphoteric/anionic surfactants and the structuring agent(s).

Measurement of the Melting Temperature

A 5 mg sample of the structuring agent is placed in a crucible. The temperature is brought to equilibrium at 20° C. for 10 min. The sample is heated in a first temperature rise from 20° C. to 80° C. at a heating rate of 20° C./minute, and is then cooled from 80° C. to −10° C. at a cooling rate of 20° C./minute. As the temperature rises, the sample absorbs heat and its physical aspect changes from solid to liquid. This absorption of heat is indicated by a dip indicating the endothermic nature of the transformation. The melting point is the lowest temperature of the dip.

Evaluation of Foam Start

Foam compositions are evaluated using the following protocol:
Before products are used, hands and forearms are washed with Anios soap and then suitably rinsed with water at 38° C. with a total hardness of 8° f. The water flow is fixed between 3-4 l/min. Without shaking arm and hand, 1 g of the product is spread beginning with the hand and working along the forearm, in 15 forward-return movements.

Foam start-up is evaluated as a function of the rate at which bubbles appear (if bubbles appear during the $1^{st}$ forward/return movement, start-up is considered to be very good with a mark of 10, and if start-up only takes place during the $10^{th}$ or $15^{th}$ forward-return movements, start-up is very bad with a mark from 1 to 0). Products are considered to be different if they are separated by at least 0.5 units.

The evaluation panel is composed of at least five trained experts. Products are compared by taking the average of the five marks.

Example 1-3: According to the Invention

| INCI name | Trade name | Example1 | Example2 | Example3 |
|---|---|---|---|---|
| VASELINE OIL | MARCOL 82 | 6 | 6 | 6 |
| POLYISOBUTENE | INDOPOL H 1500 | 8 | 0 | 0 |
| GLYCERIN |  | 5 | 5 | 5 |
| PEG 14000 | POLYOX WSR 205 AMERCHOL | 0.25 | 0.25 | 0.25 |
| WATER |  | qsp 100 | qsp 100 | qsp 100 |
| ACRYLATES/VINYL NEODECANOATE CROSSPOLYMER | ACULYN 38 | 1.5 | 1.5 | 1.5 |
| COCO-BETAINE (30% MA) | TEGO BETAIN AB 1214 | 5 | 6 | 5 |
| LAURIC ACID |  | 5.5 | 5.5 | 5.5 |
| PRESERVATIVES |  | 1.45 | 1.45 | 1.45 |
| SODIUM COCOYL GLYCINATE | AMILITE GCS-12K | 5 | 6 | 5 |
| COCAMIDOPROPYL BETAINE | DEHYTON PK 45 | 6 | 7 | 6 |
| POLYQUATERNIUM-39 | MERQUAT 3330PR | 0.1 | 0.1 | 0.1 |
| POLYQUATERNIUM-6 | MERQUAT 100 | 0.3 | 0.3 | 0.3 |
| R(surfactant/structuring agent) |  | 74/26 | 77/23 | 74/26 |
| Visco T0 (Pas) |  | 1.65 Spindle 3 | 2.16 Spindle 3 | 1.95 Spindle 3 |
| δ (η0-η45)2 months (%) |  | 7.27 | 9.7 | 16.9 |
| δ (η0-η4)2 months (%) |  | 22.4 | 27.3 | 10.7 |

Examples 1 to 3 according to the invention show loss of viscosity of less than 30% after 2 months storage at 4° C. and at 45° C.

Examples 4 to 6: Influence of the R(Surfactant/Structuring Agent)

| INCI name | Trade name | Example 4 Not in invention | Example 5 Not in invention | Example 6 Not in invention |
|---|---|---|---|---|
| VASELINE OIL |  | 6 | 6 | 6 |
| POLYISOBUTENE | INDOPOL H 1500 | 8 | 8 | 8 |
| GLYCERIN |  | 5 | 5 | 5 |
| PEG 14000 | POLYOX WSR 205 AMERCHOL | 0.25 | 0.25 | 0.25 |
| WATER |  | qsp 100 | qsp 100 | qsp 100 |
| ACRYLATES/VINYL NEODECANOATE CROSSPOLYMER | ACULYN 38 | 2 | 1.5 | 1.5 |
| COCO-BETAINE | TEGO BETAIN AB 1214 | 5 | 6 | 5 |
| LAURIC ACID |  | 3.3 | 3 | 0 |
| PRESERVATIVES |  | 1.45 | 1.45 | 1.45 |
| SODIUM COCOYL GLYCINATE | AMILITE GCS-12K | 5 | 5 | 5 |
| COCAMIDOPROPYL BETAINE | DEHYTON PK 45 | 6.6 | 6 | 6 |
| POLYQUATERNIUM-39 | MERQUAT 3330PR | 0.1 | 0.1 | 0 |
| POLYQUATERNIUM-6 | MERQUAT 100 | 0.3 | 0 | 0 |
| POLYQUATERNIUM-7 | MERQUAT 7SPR | 0 | 0 | 0.05 |
| R(surfactant/structuring agent) |  | 83/17 | 85/15 | 100/0 |
| Visco T0 (Pas) |  | 8.55 spindle 4 | 7.30 spindle 4 | 0.98 spindle 3 |
| δ (η0-η45)2 months (%) |  | 78 | 89 | Phase shift |
| δ (η0-η4)2 months (%) |  | 78 | Phase shift | Phase shift |

Examples 5 to 6 are included in the invention and their R(surfactant/structuring agent) ratio is outside the 80/20 to 60/40 range. Their loss of viscosity after 2 months storage at 4° C. and 45° C. is more than 30%, possibly leading to a macroscopic phase shift.

Example 7-8: Other Structuring Agents

| INCI name | Trade name | Example 1 According to the invention | Example 7 Not in invention | Example 8 Not in invention |
|---|---|---|---|---|
| VASELINE OIL | | 6 | 6 | 6 |
| POLYISOBUTENE | INDOPOL H 1500 | 8 | 8 | 0 |
| GLYCERIN | | 5 | 5 | 5 |
| PEG 14000 | POLYOX WSR 205 AMERCHOL | 0.25 | 0.25 | 0.25 |
| WATER | | qsp 100 | qsp 100 | qsp 100 |
| ACRYLATES/VINYL NEODECANOATE CROSSPOLYMER | ACULYN 38 | 1.5 | 1.5 | 1.5 |
| COCO-BETAINE | TEGO BETAIN AB 1214 | 5 | 5 | 5 |
| LAURIC ACID (PF: 43° C.) | LAURIC ACID 98 | 5.5 | 0 | 0 |
| STEARIC ACID (PF: 68.8° C.) | NACOL 16-98 | 0 | 5.5 | 0 |
| OLEIC ACID (PF: 13.4° C.) | NOURACID 1880 | 0 | 0 | 5.5 |
| PRESERVATIVES | | 1.2 | 1.45 | 1.45 |
| SODIUM COCOYL GLYCINATE | AMILITE GCS-12K | 5 | 5 | 5 |
| COCAMIDOPROPYL BETAINE | DEHYTON PK 45 | 6 | 6 | 6 |
| POLYQUATERNIUM-39 | MERQUAT 3330PR | 0.1 | 0.1 | 0.1 |
| POLYQUATERNIUM-6 | MERQUAT 100 | 0.3 | 0.3 | 0.3 |
| R(TA/structuring agent) | | 74/26 | 74/26 | 74/26 |
| Visco T0 (Pas) | | 1.650 Spindle 3 | 0.940 Spindle 3 | 0.173 Spindle 2 |
| $\delta$ ($\eta 0-\eta 45$)2 months (%) | | 7.27 | Phase shift | Phase shift |
| $\delta$ ($\eta 0-\eta 4$)2 months (%) | | 22.4 | 77 | Phase shift |

Structuring agents other than lauric acid with a melting point of more than 45 or unsaturated have a negative impact on the stability with a phase shift observed in most cases even for (surfactant/structuring agent) ratios between 20/80 and 40/60.

Examples 9-12: Impact of the Nature of Oil

| INCI name | Trade name | Example 3 according to the invention | Example 9 not in invention | Example 10 not in invention | Example 11 not in invention | Example 12 not in invention |
|---|---|---|---|---|---|---|
| VASELINE OIL | | 6 | 0 | 0 | 0 | 0 |
| POLY(LINSEED OIL) | RADIA 8526 | 0 | 6 | 0 | 0 | 0 |
| *BUTYROSPERMUM PARKII* BUTTER | LIPEX 202 | 0 | 0 | 6 | 0 | 0 |
| CAPRYLIC/CAPRIC TRIGLYCERIDE | MYRITOL 318 | 0 | 0 | 0 | 6 | 0 |
| OCTYLDODECANOL | EUTANOL G | 0 | 0 | 0 | 0 | 6 |
| GLYCERIN | | 5 | 5 | 5 | 5 | 5 |
| PEG 14000 | POLYOX WSR 205 AMERCHOL | 0.25 | 0.25 | 0.25 | 0.25 | 0.25 |
| WATER | | qsp 100 | qsp 100 | qsp 100 | qsp 100 | qsp 100 |
| ACRYLATES/VINYL NEODECANOATE CROSSPOLYMER | ACULYN 38 | 1.5 | 1.5 | 1.5 | 1.5 | 1.5 |
| COCO-BETAINE | TEGO BETAIN AB 1214 | 5 | 5 | 5 | 5 | 5 |

-continued

| INCI name | Trade name | Example 3 according to the invention | Example 9 not in invention | Example 10 not in invention | Example 11 not in invention | Example 12 not in invention |
|---|---|---|---|---|---|---|
| LAURIC ACID | | 5.5 | 5.5 | 5.5 | 5.5 | 5.5 |
| PRESERVATIVES | | 1.45 | 1.45 | 1.45 | 1.45 | 1.45 |
| SODIUM COCOYL GLYCINATE | AMILITE GCS-12K | 5 | 5 | 5 | 5 | 5 |
| COCAMIDOPROPYL BETAINE | DEHYTON PK 45 | 6 | 6 | 6 | 6 | 6 |
| POLYQUATERNIUM-39 | MERQUAT 3330PR | 0.1 | 0.1 | 0.1 | 0.1 | 0.1 |
| POLYQUATERNIUM-6 | MERQUAT 100 | 0.3 | 0.3 | 0.3 | 0.3 | 0.3 |
| R (surfactant/structuring agent) | | 74/26 | 74/26 | 74/26 | 74/26 | 74/26 |
| Visco T0 (Pas) | | 1.95 Spindle 3 | 1.95 Spindle 3 | 1.74 Spindle 3 | 1.57 Spindle 3 | 1.32 Spindle 3 |
| $\delta$ ($\eta 0-\eta 45$) 2 months (%) | | 16.9 | 41 | 41 | 26.7 | 32 |
| $\delta$ ($\eta 0-\eta 4$) 2 months (%) | | 10.7 | 6.6 | 41 | 40 | 20 |

These examples show that the presence of a non-volatile hydrocarbon type oil such as Vaseline oil possibly with polyisobutene can keep the loss of viscosity to less than 30% unlike what happens with the use of oils such as POLY (LINSEED OIL), BUTYROSPERMUM PARKII BUTTER, CAPRYLIC/CAPRIC TRIGLYCERIDE, OCTYLDODECANOL.

Example 13-14: Association of Glycinate and Another Surfactant

| INCI name | Trade name | Example 1 according to the invention | Example 13 according to the invention | Example 14 according to the invention |
|---|---|---|---|---|
| VASELINE OIL | | 6 | 6 | 6 |
| POLYISOBUTENE | INDOPOL H 1500 | 8 | 8 | 8 |
| GLYCERIN | | 5 | 5 | 5 |
| PEG 14000 | POLYOX WSR 205 AMERCHOL | 0.25 | 0.25 | 0.25 |
| WATER | | qsp 100 | qsp 100 | qsp 100 |
| ACRYLATES/VINYL NEODECANOATE CROSSPOLYMER | ACULYN 38 | 1.5 | 1.5 | 1.5 |
| COCO-BETAINE | TEGO BETAIN AB 1214 | 5 | 5 | 5 |
| LAURIC ACID | | 5.5 | 5.5 | 5.5 |
| PRESERVATIVES | | 1.45 | 1.45 | 1.45 |
| SODIUM COCOYL GLYCINATE | AMILITE GCS-12K | 5 | 2.5 | 2.5 |
| SODIUM LAUROYL METHYL ISETHIONATE | ISELUX LQ-CLR-SB | 0 | 2.5 | 0 |
| SODIUM LAURYL SULFOACETATE | LATHANOL LAL | 0 | 0 | 2.5 |
| COCAMIDOPROPYL BETAINE (38% MA) | DEHYTON PK 45 | 6 | 6 | 6 |
| POLYQUATERNIUM-39 | MERQUAT 3330PR | 0.1 | 0.1 | 0.1 |
| POLYQUATERNIUM-6 | MERQUAT 100 | 0.3 | 0.3 | 0.3 |
| R(surfactant/structuring agent) | | 74/26 | 74/26 | 74/26 |
| Visco T0 (Pas) | | 1.65 Spindle 3 | 1.44 Spindle 3 | 1.53 Spindle 3 |
| $\delta$ ($\eta 0-\eta 45$) 2 months (%) | | 7.27 | 23 | 16 |
| $\delta$ ($\eta 0-\eta 4$) 2 months (%) | | 22.4 | 11 | 16 |

The presence of at least 50% of a glycinate type surfactant can limit the stability such that the loss of viscosity is less than 30%.

Comparative Tests Between Example 1 and
Examples 15 and 16: Replacement of Glycinate

| INCI NAME | Trade name | Example 1 according to the invention | Example 15 not in invention | Example 16 not in invention |
|---|---|---|---|---|
| VASELINE OIL | | 6 | 6 | 6 |
| POLYISOBUTENE | INDOPOL H 1500 | 8 | 0 | 0 |
| GLYCERIN | | 5 | 5 | 5 |
| PEG 14000 | POLYOX WSR 205 AMERCHOL | 0.25 | 0.25 | 0.25 |
| WATER | | 15.5 | 18.17 | 21.72 |
| ACRYLATES/VINYL NEODECANOATE CROSSPOLYMER | ACULYN 38 | 1.5 | 1.5 | 1.5 |
| COCO-BETAINE | TEGO BETAIN AB 1214 | 5 | 5 | 5 |
| LAURIC ACID | | 5.5 | 5.5 | 5.5 |
| PRESERVATIVES | | 1.45 | 1.45 | 1.45 |
| SODIUM LAUROYL METHYL ISETHIONATE | ISELUX | 0 | 5 | 0 |
| SODIUM LAURETH SULFATE | TEXAPON N 702 | 0 | 0 | 5 |
| SODIUM COCOYL GLYCINATE | AMILITE GCS-12K | 5 | 0 | 0 |
| COCAMIDOPROPYL BETAINE (38% MA) | DEHYTON PK 45 | 6 | 6 | 6 |
| POLYQUATERNIUM-39 | MERQUAT 3330PR | 0.1 | 0.1 | 0.1 |
| POLYQUATERNIUM-6 | MERQUAT 100 | 0.3 | 0.3 | 0.3 |
| R(surfactant/structuring agent) | | 74/26 | 74/26 | 74/26 |
| Visco T0(Pas) | | 1.65 Spindle 3 | 0.54 Spindle 3 | 1.4 Spindle 3 |
| δ (η0-η45)2 months (%) | | 7.27 | 8 | 55.71 |
| δ (η0-η4)2 months (%) | | 22.4 | 40.74 | 32.8 |
| Foam start | | 9.3 +/− 0.94 | 2.5 +/− 1.12 | 5.7 +/− 0.94 |

Example 1 according to the invention containing glycinate (unlike the other examples 13 and 14 that do not) has a stable viscosity at 4° C. and 45° C. after 2 months storage (loss of viscosity less than 30%) and foam start performances are better.

The invention claimed is:

1. A composition comprising at least the following in a physiologically acceptable medium:
   an aqueous phase and;
   an oily phase comprising at least one non-volatile hydrocarbon oil chosen from among linear or branched hydrocarbons, said non-volatile hydrocarbon oil being chosen from among paraffin oils and derivatives thereof, vaseline oil, polydecenes, polybutenes, polyisobutenes, hydrogenated polyisobutenes and squalene, and;
   at least one anionic glycinate surfactant and possibly at least one additional anionic surfactant different from glycinates and fatty acid salts;
   at least one amphoteric or zwitterionic surfactant and;
   at least 5% by weight of the total weight of the composition of at least one structuring agent chosen from among saturated fatty acids with a melting point of less than 45° C., saturated fatty alcohols with a melting point of less than 45° C., and mixtures thereof and;
   the ratio by weight of the total quantity of anionic surfactants and amphoteric or zwitterionic surfactants to the quantity of the structuring agent varies between 80/20 and 60/40.

2. The composition, according to claim 1, wherein the ratio by weight between the anionic surfactant(s) and the amphoteric surfactant(s) is between 20/80 and 75/25.

3. The composition, according to claim 1, wherein the structuring agent is chosen from among saturated fatty acids with a melting point of more than 20° C. and less than 45° C. and saturated fatty alcohols in C8-C24 with a melting point of more than 20° C. and less than 45° C. and mixtures thereof.

4. The composition, according to claim 3, wherein the structuring agent is lauric acid and/or lauric alcohol.

5. The composition, according to claim 1, wherein the anionic glycinate surfactant is chosen from among glycinate alkyls with the following chemical formula:

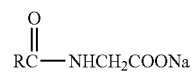

where R is an alkyl chain with 8 to 16 carbon atoms and mixtures thereof.

6. The composition, according to claim 1, wherein the content of the anionic glycinate surfactant is at least 30% by weight of the total weight of the anionic surfactant(s) present in the composition.

7. The composition, according to claim 1, wherein the additional anionic surfactant(s) are chosen from among acyl glutamates, isethionate alkyls, sulfosuccinate alkyls, sulfoacetate alkyls, taurate alkyls, sulfate alkyls and ether sulfate alkyls and mixtures thereof.

8. The composition, according to claim 1, wherein the amphoteric or zwitterionic surfactants are chosen from among alkylbetaines and alkylamidopropylbetaines and mixtures thereof.

9. The composition, according to claim 1, wherein the concentration of amphoteric or zwitterionic surfactants is more than 5% by weight of the total weight of the composition.

10. The composition, according to claim 1, wherein the total concentration of anionic surfactants, amphoteric surfactants and fatty acid and/or fatty alcohol varies from 12% to 33% by weight of the total weight of the composition.

11. The composition, according to claim 1, also containing at least one thickening agent.

12. The composition, according to claim 1, which is an oil-in-water emulsion.

13. A cosmetic method for cleansing keratin materials or for makeup removal for keratin materials, said method comprising applying on a keratin material a composition as defined according to claim 1.

14. A cosmetic method of cleaning dirt residues of human keratin materials, wherein a composition according to claim 1 is applied on said keratin materials, in the presence of water, and massage is performed to create a foam and the foam formed and the dirt residues are eliminated by rinsing with water.

15. The composition, according to claim 2, wherein the structuring agent is chosen from among saturated fatty acids with a melting point of more than 20° C. and less than 45° C. and saturated fatty alcohols in C8-C24 with a melting point of more than 20° C. and less than 45° C. and mixtures thereof.

16. The composition, according to claim 2, wherein the ratio by weight between the anionic surfactant(s) and the amphoteric surfactant(s) is between 25/75 and 55/45.

17. The composition, according to claim 3, wherein the anionic glycinate surfactant is chosen from among glycinate alkyls with the following chemical formula:

where R is an alkyl chain with 8 to 16 carbon atoms and mixtures thereof.

18. The composition, according to claim 4, wherein the anionic glycinate surfactant is chosen from among glycinate alkyls with the following chemical formula:

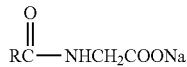

where R is an alkyl chain with 8 to 16 carbon atoms and mixtures thereof, and the non-volatile hydrocarbon oil is chosen from among paraffin oils and derivatives thereof.

19. The composition, according to claim 2, wherein the anionic glycinate surfactant is chosen from among glycinate alkyls with the following chemical formula:

where R is an alkyl chain with 8 to 16 carbon atoms and mixtures thereof.

* * * * *